United States Patent [19]

Hildon et al.

[11] 4,168,274

[45] * Sep. 18, 1979

[54] PRODUCTION OF A PERACID AND AN OXIRANE

[75] Inventors: Anthony M. Hildon, Tattenhall; Peter F. Greenhalgh, Widnes, both of England

[73] Assignee: Interox Chemicals Limited, London, England

[ * ] Notice: The portion of the term of this patent subsequent to Jan. 31, 1995, has been disclaimed.

[21] Appl. No.: 806,597

[22] Filed: Jun. 14, 1977

Related U.S. Application Data

[63] Continuation-in-part of Ser. No. 649,747, Jan. 16, 1976, Pat. No. 4,071,541.

[30] Foreign Application Priority Data

Feb. 4, 1975 [GB] United Kingdom ............... 4692/75
Feb. 12, 1977 [GB] United Kingdom ............... 5695/77
Apr. 7, 1977 [GB] United Kingdom ............. 14902/77

[51] Int. Cl.$^2$ .................. C07D 301/14; C07C 179/12; C07C 179/10
[52] U.S. Cl. ........................... 260/348.25; 260/502 R
[58] Field of Search ..................... 260/348.25, 502 R

[56] References Cited

U.S. PATENT DOCUMENTS 3,799,949  3/1974  Keller et al. .................. 260/348.5 L

FOREIGN PATENT DOCUMENTS 2141156  3/1973  Fed. Rep. of Germany .
2262970  7/1974  Fed. Rep. of Germany .
1188791  4/1970  United Kingdom .

Primary Examiner—Norma S. Milestone
Attorney, Agent, or Firm—Larson, Taylor and Hinds

[57] ABSTRACT

The invention provides a continuous process for the production of a peracid in an organic solvent comprising the steps of: (a) providing an aqueous phase comprising sulphuric acid, hydrogen peroxide and water; (b) providing an organic phase comprising an organic solvent and carboxylic acid; and (c) contacting said aqueous and organic phases countercurrently to produce an aqueous solution comprising sulphuric acid and water and an organic product solution comprising organic solvent and a peracid corresponding to said carboxylic acid. Desirably the process includes the added step of: (d) utilizing at least a portion of said aqueous solution to provide at least a portion of the aqueous phase of step (a). The invention also provides a continuous process for the epoxidation of an alkene comprising steps (a) through (d) with the added steps of: (e) reacting at least a portion of the peracid of said organic solution and an alkene to produce a product mixture comprising oxirane, carboxylic acid and organic solvent; (f) effecting distillation of said product mixture to produce a product phase comprising the oxirane and a recycle phase comprising carboxylic acid and organic solvent; and (g) utilizing at least a portion of said recycle phase to form at least a portion of the organic phase of step (b).

20 Claims, 3 Drawing Figures

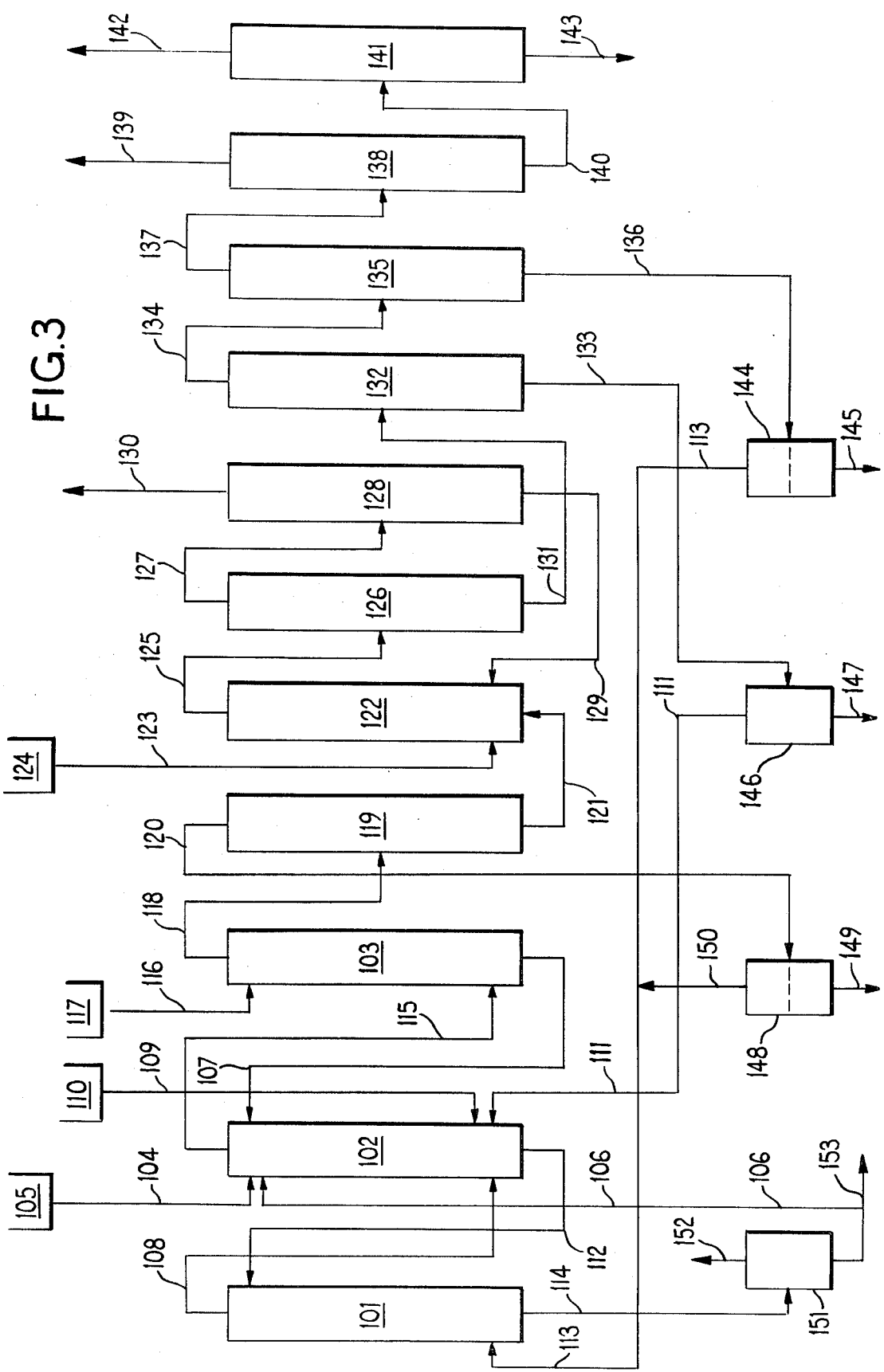

PRODUCTION OF A PERACID AND AN OXIRANE

CROSS-REFERENCES TO RELATED APPLICATIONS

This application is a continuation-in-part of our copending application Ser. No. 649,747 filed Jan. 16, 1976, now U.S. Pat. No. 4,071,541, issued Jan. 31, 1978, the disclosure of which is incorporated herein by reference.

BACKGROUND OF THE INVENTION

The present invention relates to the preparation of peracids (by which we mean herein peroxycarboxylic acids) and the use of such peracids in the epoxidation of alkenes, especially lower alkenes.

DESCRIPTION OF THE PRIOR ART

The general preparation of peracids by the reaction of a carboxylic acid with hydrogen peroxide in an aqueous medium is well known. It is also known that such peracids can be extracted into organic solvents. Finally it is known that peracids can be used to make oxiranes.

SUMMARY OF THE INVENTION

It is one object of the present invention to provide a novel continuous process for the production of a peracid in an organic solvent.

Accordingly the present invention provides a continuous process for the production of a peracid in an organic solvent comprising the steps of:
(a) providing an aqueous phase comprising sulphuric acid, hydrogen peroxide and water;
(b) providing an organic phase comprising an organic solvent and carboxylic acid; and
(c) contacting said aqueous and organic phases countercurrently to produce an aqueous solution comprising sulphuric acid and water and an organic product solution comprising organic solvent and a peracid corresponding to said carboxylic acid.

Desirably the process includes the further step of:
(d) utilising at least a portion of said aqueous solution to provide at least a portion of the aqueous phase of step (a).

It is another object of the present invention to provide a novel continuous process for the epoxidation of an alkene utilising a more efficient process for the production of the peracid than heretofore.

Accordingly the present invention also provides a continuous process for the epoxidation of an alkene by reaction with a peracid to produce an oxirane, comprising the cyclic steps of:
(a) providing an aqueous phase comprising sulphuric acid, hydrogen peroxide and water;
(b) providing an organic phase comprising a carboxylic acid and an organic solvent;
(c) contacting said aqueous and organic phases countercurrently to produce an aqueous solution comprising sulphuric acid and water and an organic solution comprising peracid and organic solvent;
(d) utilizing at least a portion of said aqueous solution to provide at least a portion of the aqueous phase of step (a);
(e) reacting at least a portion of the peracid of said organic solution and an alkene to produce a product mixture comprising oxirane, carboxylic acid and organic solvent;
(f) effecting distillation of said product mixture to produce a product phase comprising the oxirane and a recycle phase comprising carboxylic acid and organic solvent; and
(g) utilising at least a portion of said recycle phase to form at least a portion of the organic phase of step (b).

Further and subsidiary objects of the invention will appear hereinafter.

It should be noted that the product of an epoxidation reaction is called an "oxirane" or "epoxide", which terms are synonymous.

SELECTION OF THE CARBOXYLIC ACID

As used herein, the term "carboxylic acid" has its normal meaning but it is necessary to emphasise that in practising the invention a proper selection of the "carboxylic acid", "organic solvent" and "alkene" is desirable in order to provide optimum efficiencies. However with the guide lines given herein such selection is within the ability of one skilled in the art.

As will be understood from the statement of the invention given above, the carboxylic acid is caused to react with hydrogen peroxide to give a peracid which then reacts with the alkene to give an oxirane and regenerate the carboxylic acid. It is therefore necessary to select a carboxylic acid such that it and the peracid are sufficiently soluble in water to permit the reaction to take place and also to be soluble in the organic solvent. Moreover the carboxylic acid and peracid should not undergo undesirable side reactions and, for example, should not unduly catalyse ring splitting of the oxirane. For these reasons we prefer to use unsubstituted monocarboxylic acids having at least two but less than six carbon atoms. Within these guide lines substituted, e.g. halogen-substituted, carboxylic acids such as β-chloropropionic acid may be used, but the strength of such acids and the possibility of their reaction or introduction of chloride species may render them less desirable. Di- and polycarboxylic acids seem to offer no advantages, and may be undesirable since a product mixture containing them cannot readily be distilled to produce the recycle phase without substantial degradation.

The preferred carboxylic acids are therefore acetic and propionic acid.

SELECTION OF THE SOLVENT

As to the organic solvent, its prime function is to set up a discrete organic phase in which the carboxylic acid and peracid are soluble. There are additional criteria for selecting the organic solvent in addition to its solvent powers, namely a low solvent power for water, a low solubility in aqueous sulphuric acid, non-reactivity under the conditions of the reaction in the presence of the other reactants. However in practice one of the most important criteria is the ease with which the solvent can be separated from the product and by-products, preferably by distillation. It is however important to note that it need not be separable from the carboxylic acid and peracids. It will be understood that although various solvents are listed herein, the selection of a solvent for practical use must depend on the precise process and reactants.

The solvent may be a halogenated, e.g. fluorinated or chlorinated, aliphatic hydrocarbon for example: dichloromethane, trichloromethane, tetrachloromethane, chloroethane, 1,1-dichloroethane, 1,2-dichloroethane, 1,1,1-trichloroethane, 1,1,2-trichloroethane, 1,1,1,2-tetrachloroethane, 1,1,2,2-tetrachloroethane, 1-chloropropane, 2-chloropropane, 1,1-dichloropropane, 1,2-dichloropropane, 1,3-dichloropropane, 2,2-dichloropropane, 1,1,1-trichloropropane, 1,1,2-trichloropropane, 1,1,3-trichloropropane, 1,2,2-trichloropropane, 1,2,3-trichloropropane, tetrachloropropanes, or chloro-substituted butanes, pentanes or hexanes.

The solvent may be a chlorinated aromatic or cycloaliphatic hydrocarbon, for example:
chlorobenzene, cyclohexylchloride.

Chlorinated hydrocarbons, although normally considered very inert, may give rise to chloride species, which in the presence of water and/or sulphuric acid can be very corrosive. It may therefore be desirable to select the solvent from among non-chlorinated hydrocarbons, such as aliphatic hydrocarbons, cycloaliphatic hydrocarbons, aromatic hydrocarbons and alkylaryl hydrocarbons for example:
decane, heptane,
cyclohexane,
benzene,
toluene, xylene Other solvents, known generally in the art of peracids may be used, such as:
esters, for example, ethyl acetate, diethyl phthalate, di-n-butyl phthalate, ethyl propionate
nitro compounds, for example, nitrobenzene, benzonitrile ethers for example di-n-propyl ether.

A solvent mixture can be used, for example that known as petroleum ether which is a mixture of aliphatic hydrocarbons.

It is not theoretically necessary that the organic solvent should be a saturated compound provided that any unsaturation is not epoxidisable under the conditions of the process.

PRODUCTION OF THE PERACID

It is now convenient to develop, in general terms, steps (a) through (d) of the invention as defined generally.

A liquid/liquid contacting device is used and this may comprise any of these devices known in the art arranged to operate in countercurrent. Specific examples are columns, including sieve plate, bubble-cap, stirred and pulsed columns, and a countercurrent series of mixer settlers or any combination. To this contacting device is passed an aqueous phase comprising sulphuric acid, hydrogen peroxide and water and an organic phase comprising carboxylic acid and organic solvent.

It is a secondary object of the invention to provide a process which is inherently more efficient, in terms of conversion per pass, than known prior processes.

Thus in effecting the instant process, the components will partition between the two phases and, in the aqueous phase, the reaction of hydrogen peroxide with carboxylic acid to give peracid will be catalysed by the sulphuric acid. This reaction is normally slow to reach equilibrium but is accelerated in the present invention by the extraction of the peracid into the organic phase. Indeed operating the contacting device in countercurrent enables better than 90% conversion of the hydrogen peroxide into peracid to be obtained. The process is therefore clearly and surprisingly more efficient in terms of total conversion and conversion per pass than the hitherto known process of effecting the reaction in the aqueous phase, allowing the aqueous reaction mixture to reach equilibrium and then extracting the equilibrium mixture with a solvent.

Furthermore, operation in countercurrent effectively limits the maximum concentrations of the organic reactants in the aqueous phase so that any risk of explosion is minimised, operation of the known two stage process being known to be potentially hazardous.

In addition to its function as catalyst, the sulphuric acid also has the function of adjusting the specific gravity of the aqueous phase to assist separation of the phases. The relative specific gravities of the organic and aqueous phases will determine their direction of movement in countercurrent operation in a column. However care should be taken, as is known, that the concentration of the sulphuric acid is maintained so as to be sufficient for catalysis but insufficient to cause degradation of any of the organic components by dehydration, etc.

The aqueous solution removed from the contacting device has, in effect, had some or all of its hydrogen peroxide replaced by water. It is therefore desirably concentrated by the removal of water and recycled after addition of hydrogen peroxide.

It is worth commenting that although the theoretical ratio of hydrogen peroxide to carboxylic acid is 1:1 by moles, it is often desirable in chemical operations to have an excess of one reactant. Preferably the instant reaction is effected with an excess of carboxylic acid to ensure maximum reaction of hydrogen peroxide and so avoid the known problems of effectively recovering the hydrogen peroxide from the aqueous solution being concentrated.

THE EPOXIDATION REACTION

Turning now to steps (e) and (f) of the invention as stated, the organic solution of peracid is reacted, without prior separation of peracid, with an alkene to give an oxirane.

SELECTION OF THE ALKENE

The term "alkene" is used herein to mean an epoxidisable compound containing an olefinic double bond, i.e., the group $>C=C<$. The term includes di- or polyunsaturated and/or substituted compounds where such di- or polyunsaturation and/or substitution will not prevent epoxidation.

Although the present invention can be applied to ethylene, the lowest alkene, it is not thought that the reaction would be economically attractive at the present time as compared with the direct oxidation of ethylene. However it might be economically suitable for substituted ethylenes, e.g. phenylethylene (i.e., styrene). It would appear that the invention is likely to prove most advantageous when applied to propylene and chloro- or hydroxyl-substituted propylene. Propylene is otherwise known as propene; the chloro-substituted compound is allyl chloride or 3-chloropropene and the hydroxyl-substituted compound is allyl alcohol or 2-propen-1-ol. Throughout this specification the term "propene" will be used to include these substituted compounds and the terms "propylene", "allyl chloride" and "allyl alcohol" will refer to the specific compounds. It will be apparent that the corresponding oxirane to propene is epoxypropane, while propylene oxide, epichlorohydrin and glycidol correspond, respectively, to the specific compounds just mentioned.

The invention also appears to be economically attractive when applied to butenes. The term "butene" is intended to include both straight and branched chain isomers and internal and external olefins together with their substituted derivatives.

The invention can also be applied to the various pentenes and to higher alkenes such as octene, decene, tetradecene, hexadecene, octadecene, dodecene and eicosene.

Cyclic alkenses can also be used such as cyclopentene, cyclohexane and alkyl cyclohexenes.

Such polyunsaturated compounds as butadiene, pentadiene, hexadiene, vinyl cyclohexene and polybutadiene can also be used.

In addition to substituted alkenes as normally understood the invention can be applied to ethers, esters, ketones etc., containing an olefinic double bond but it will be realised that additional oxidation reactions may take place.

Normally, in addition to the other criteria used, the solvent will be selected to be a solvent for the alkene and probably the oxirane.

It will be observed that by using an organic solution of the peracid, water and sulphuric acid are not brought into contact with the oxirane so ring opening is reduced. If desired, the organic solution from step (c) can be dried before step (e), as by distillation to remove water, conveniently as an azeotrope. Moreover if carry over of acidic species is a disadvantage for this or other reasons, the organic solution of peracid may be washed with a small amount of water in substitution for or in addition to drying. If necessary microfiltration or other similar techniques can be used to remove entrained water.

PRODUCTION OF PERACID—GENERAL CONDITIONS

Dealing with the process of this invention in more detail and as applied specifically to the preparation and use of perpropionic acid, an aqueous phase is supplied to the extraction device, e.g. the upper part of an extraction column, to pass downwardly therethrough. This aqueous phase comprises sulphuric acid, hydrogen peroxide and water. The proportion of sulphuric acid is preferably approximately 40% by weight and is desirably between 30% and 60% by weight. If a lower yield is acceptable then the proportion of sulphuric acid can be between 15% and 85%. Conveniently however for operating reasons the sulphuric acid is derived from 75% by weight sulphuric acid solution in water which forms a feedback from the purification stages which will be described hereinafter, together with make-up acid. It should be recalled that the specific gravity of the aqueous phase will depend largely on the concentration of sulphuric acid.

The hydrogen peroxide is conveniently approximately 29% by weight of the aqueous phase and in practice between 10% and 35% is very satisfactory. If lower yields are acceptable, then as little as 5% could be used, but above about 35% the mixture could be hazardous. This hydrogen peroxide is very conveniently supplied as approximately 70% by weight solution in water.

Water makes up the third component of the aqueous phase and its proportions can readily be found by difference.

The organic phase is fed into the lower part of the extraction column to pass upwardly in countercurrent with the aqueous phase and comprises, for the production of perpropionic acid, a solution of propionic acid in an organic solvent. The concentration of propionic acid is desirably 20% or preferably between 15% and 30% of the organic phase or conveniently between 10% and 50% by weight.

The relative volumes of the aqueous and organic phases and their concentrations together set the ratio between hydrogen peroxide and propionic acid. This ratio is theoretically 1:1 by moles but is conveniently 1:1.4 and may be from 1:0.5 to 1:4, or, if low conversions are acceptable, from 1:0.1 to 1:10. However if an excess of hydrogen peroxide is used, it will appear in the effluent from the extraction column and this may be undesirable; the mole ratio is therefore preferably 1:>1.

The function of the organic solvent is to extract the perpropionic acid from the aqueous phase in which it is formed by reaction between the hydrogen peroxide and propionic acid extracted from the organic phase into the aqueous phase. The effect of this is to shift the equilibrium in favour of formation of perpropionic acid. Thus in a two stage process in which the propionic acid is reacted in an aqueous system with hydrogen peroxide and the resultant peracid extracted into an organic solvent all under optimum conditions, it is only possible to achieve about 66% conversion of propionic acid or hydrogen peroxide to perpropionic acid. However using the process of this invention, over 90% conversion of hydrogen peroxide to perpropionic acid can be obtained. In consequence the process of this invention is very much more efficient and therefore more effective in terms of plant utilisation.

It may be convenient to carry out a further extraction of the aqueous phase leaving the base of the extraction column using fresh organic solvent in order to extract substantially all of both propionic acid and perpropionic acid from the aqueous effluent. It will be understood that in accordance with known extraction techniques, this further extraction can in fact be carried out in the same extraction column. It may also be convenient to use the upper part of the extraction column, or a separate column, to effect a backwash operation on the organic phase in order to remove dissolved hydrogen peroxide. This can be effected by dividing the aqueous feed to the column into two portions, one being primarily dilute sulphuric acid and the other primarily hydrogen peroxide, and introducing these two portions at spaced locations in the column.

Two side reactions could in theory occur in the extraction column, namely the reaction of hydrogen peroxide with sulphuric acid to form Caro's acid and the reaction of propionic acid with perpropionic acid to give propionyl peroxide. However the simultaneous extraction into the organic phase has the general effect of minimising these side reactions as compared with the two stage process and the process of the present invention is also much safer than the said two stage process which is subject to an explosion hazard.

The reaction of the present invention proceeds naturally at a satisfactory rate so that operation at natural temperatures is satisfactory. Natural temperature is to some extent dependant on a scale effect since only little heat is evolved on mixing and reaction. Since the reaction is not markedly temperature sensitive no special steps are needed and a column temperature of 20°–25° C. is satisfactory.

In selecting the various reactants for the production of the peracid, it is necessary to remember that the reaction system is dynamic rather than static. In consequence although individual parameters can be measured in static conditions, the dynamic interactions cause considerable differences.

Thus the present invention utilises the following reactions:

Carboxylic Acid + H$_2$O$_2$ → Peracid + Water

Peracid (aqueous) + Solvent → Peracid (org.) + Water

Peracid (org) + Alkene → Epoxide + Carboxylic acid

If the first reaction is carried out in isolation and with a molar ratio propionic acid: hydrogen peroxide = 1.4:1, the equilibrium constant corresponds to about 60% conversion.

If the second reaction is carried out using 1:1 volume ratio the distribution coefficient corresponds to about 70% extraction of the perpropionic acid. In effect this means an efficiency calculated as proportion of hydrogen peroxide reacted to give peracid in organic solution of 60% × 70% = 42%.

In the prior process described in German OLS 2141156 continuous countercurrent extraction of the aqueous phase was employed. This corresponds (in theory) to a series of separate extractions each of 70% efficiency. In practice about 4 theoretical stages (of 100% equilibration) would be used so as to give a total of 99.2% extraction and a final concentration of peracid in the organic phase of about 22%. The maximum theoretical overall efficiency can however only be 60%.

The present invention uses in effect a series of separate stages for the first reaction, each one coupled with a series of extractions. Clearly the equilibrium constants are the same, but the actual efficiency of the process described with reference to FIG. 1 hereof is 93%; the theoretical efficiency could be even higher with further stages.

There is in addition, the advantage that the recycled aqueous solution contains only about 7% of the hydrogen peroxide. Since on concentration there is an inevitable loss of hydrogen peroxide equivalent to about 10% of the content of the stream being concentrated, the loss in the present system is of the order of 0.7% of the hydrogen peroxide fed per pass whereas in the said prior proposal it is about 4%.

As a guide to the selection of a reactant/solvent system for the production of the peracid, reference should be made to Table I which shows some relevant data.

TABLE I

| | pK × 10$^5$ | boiling point °C. | density | solubility in water |
|---|---|---|---|---|
| Carboxylic acids | | | | |
| formic | 17.7 | 101 | 1.22 | ∞ |
| acetic | 1.8 | 118 | 1.04 | ∞ |
| propionic | 1.3 | 141 | 0.99 | ∞ |
| n.butyric | 1.5 | 163 | 0.96 | ∞ |
| caproic | 1.4 | 205 | 0.93 | δ |
| n.heptoic | 1.3 | 223 | 0.92 | δ |
| chloracetic | 140 | 189 | 1.40 | v |
| α-chlorpropionic | 147 | 186 | 1.28 | ∞ |
| β-chlorpropionic | 10 | 204 | — | s |
| Solvents | | | | |
| chloroethane | | 13.1 | 0.90 | δ |
| tetrachloroethane | | 146 | 1.60 | δ |
| propylene dichloride | | 96 | 1.16 | δ |
| chlorobenzene | | 132 | 1.11 | i |
| cyclohexylchloride | | 142 | 100 | i |
| decane | | 174 | 0.73 | i |
| heptane | | 98 | 0.68 | i |
| cyclohexane | | 81 | 0.78 | i |

TABLE I-continued

| | pK × 10$^5$ | boiling point °C. | density | solubility in water |
|---|---|---|---|---|
| benzene | | 80.1 | 0.88 | δ |
| toluene | | 110 | 0.87 | i |
| ethylacetate | | 77 | 0.90 | s |
| ethyl propionate | | 99 | 0.89 | δ |
| nitrobenzene | | 211 | 1.20 | δ |
| di n-propyl ether | | 91 | 0.74 | δ |
| petroleum ether | | 80–100 | 0.8 | i |

EPOXIDATION—GENERAL CONDITIONS

The solution of peracid in organic solvent is used in step (e) of the invention.

In order to effect the actual epoxidation reaction, the solution of perpropionic acid in organic solvent from the extraction column is mixed with a molar excess, conveniently of the order of 25% to 50% (although it could be lower or higher) of alkene, e.g. propene, and is then pumped to a suitable reactor, e.g. a pressurised water-cooled tubular reactor.

Temperatures in the range 50°–150° C. can be used, but we prefer to operate in the range 75°–120° C. and desirably in the range 90°–110° C. The degree of cooling is desirably adjusted so as to provide this preferred temperature. The pressurisation is sufficient to maintain the propene in solution at the chosen temperature. If an adequate residence time is allowed in this reactor, for example in excess of 20 minutes and conveniently about 25 minutes in the manufacture of propylene oxide, but depending on temperature, very nearly complete conversion of the perpropionic acid will be achieved. Thus approximately 99% of the perpropionic acid can be caused to react. Moreover the reaction is very selective and of the perpropionic acid which does react, in excess of 98% reacts to give propylene oxide and less than 2% to give byproducts. Of the side reactions which take place, the most common are the degradation of perpropionic acid into propionic acid and oxygen or into ethanol and carbon dioxide. There is in addition some formation of acetaldehyde, propionaldehyde, propylene glycol or propylene glycol esters and other side products.

The precise physical form of the reactor is not important and we visualise that cocurrent tubular reactors and continuous stirred tanks can both be used, either individually or in some combination. Multi-stage batch reactors can also be used.

PURIFICATION OF PRODUCT

The product mixture from the reactor comprises oxirane, carboxylic acid and organic solvent and is taken in step (f) to a multi-stage distillation process intended to separate out the pure product, recycle streams and the impurities. The precise details of the purification process will depend on the alkene and the relationship between its boiling point, that of the oxirane and the other constituents. Moreover the ease and effectiveness of this purification step depends on the proper choice of alkene, carboxylic acid and organic solvent as outlined above.

In the case of the production of propylene oxide from propylene, the product from the reactor is conveniently subjected to a stripping operation in order to remove unreacted propylene which is recovered and recycled to the reactor. The stripped product from the reactor is then suitable for separation by multi-stage distillation.

If in the production of propylene oxide, propylene dichloride is used as the solvent, then the following stages of distillation are appropriate.

In the first stage, the light fraction comprises the propylene oxide with low boiling point impurities such as acetaldehyde, water and some propylene dichloride. The heavy fraction from this first stage is propionic acid in propylene dichloride and this is recycled but may be distilled to remove heavy impurities such as propylene glycol. The light fraction from the first stage is re-distilled in a second stage to give a second light fraction comprising the propylene oxide, acetaldehyde and propionaldehyde and a second heavy fraction comprising water and propylene dichloride which is also recycled. Successive further distillations purify the propylene oxide.

Essentially the same purification stages can be used in the system benzene/propionic acid/propylene. However in the system propylene dichloride/propionic acid/allyl chloride, different purification stages are necessary although the effect of the purification stages is still ultimately to produce a product phase and a recycle phase. In other words, the distillation chain separates out the constituents in order of boiling point and it is convenient, but not essential, that the carboxylic acid should separate with the solvent.

RECYCLE

In accordance with step (g) the recycle phase is passed back to the extraction column as the organic phase, after the addition of organic solvent and carboxylic acid in order to make up for the small inevitable wastage and the purges. Conveniently in the case of a propylene oxide/propionic acid/propylene dichloride system, the heavy fraction from the first distillation stage (which comprises propionic acid in propylene dichloride) is used as the main feed of organic phase to the liquid/liquid contacting device and the heavy phase from the second distillation stage (which comprises propylene dichloride) is used to carry out the further extraction of the aqueous phase.

Referring now to the extraction column, it will be recalled that the aqueous phase is supplied to the upper part of the column and is withdrawn from the lower part of the column. As withdrawn from this lower part of the column, the aqueous phase comprises sulphuric acid and water together with perhaps small amounts of hydrogen peroxide, since as explained, the conditions in the extraction column are preferably such as to ensure almost complete reaction of the hydrogen peroxide. It will be recalled that the second extraction will have removed substantially all the propionic and perpropionic acid from the aqueous effluent. The dilute sulphuric acid is preferably concentrated, desirably by evaporation or distillation, in order to remove the unwanted water and then is recycled to the extraction column, in accordance with step (d).

MODIFICATIONS

The modifications necessary to convert the above generalised description relating to propylene to a description relating to any alkene will be apparent to one skilled in the art. However in order to assist in the selection of suitable carboxylic acids and organic solvents for any given alkene reference may conveniently be made to Table II hereof.

TABLE II

|  | boiling point | density |
|---|---|---|
| Alkenes | | |
| allyl chloride | 45 | 0.94 |
| butylene | −6.3 | 0.59 |
| decane | 170 | 0.74 |
| propylene | −47.8 | — |
| styrene | 145 | 0.91 |
| Epoxides | | |
| epoxy-butane | 61 | 0.84 |
| epoxy-decane | 219 | — |
| epoxy-propane | 35 | 0.86 |
| styrene oxide | 191 | 1.05 |
| epichlorhydrin | 116 | 1.18 |
| By-products | | |
| acetaldehyde | 20.8 | 0.78 |
| ethanol | 78.5 | 0.79 |
| propionaldehyde | 48.8 | 0.81 |
| propylene glycol | 189 | 1.04 |
| propylene dipropionate | 200 | |

For any solvent/carboxylic acid/alkene combination the optimum working conditions (e.g. temperatures and concentrations) may be determined by trail and experiment (or predicted from the conditions which obtain in laboratory experiments with batch processes). One factor which can be determined from batch processes is the distribution coefficient between the organic and aqueous phases for the species in question. Of course, this is only a guide, for kinetic as well as (indeed rather than) thermodynamic factors are involved. If with any solvent the resulting concentration of peracid in the organic solution is inconveniently low for a particular purpose, it may be desirable to concentrate the solution, e.g. by distillation under reduced pressure.

DESCRIPTION OF PREFERRED EMBODIMENTS

In order that the invention may more readily be understood three embodiments of the same will now be described by way of example and with reference to the accompanying drawings wherein:

FIG. 3 is a flow sheet for a modified process for the production of propylene oxide.

The present invention, being a continuous process, is best described with reference to the concentration of reactants flowing in various parts of the system. The figures given correspond to a pilot scale operation but it will be readily understood by those skilled in the art how to scale up to any desired degree.

Figure 1:
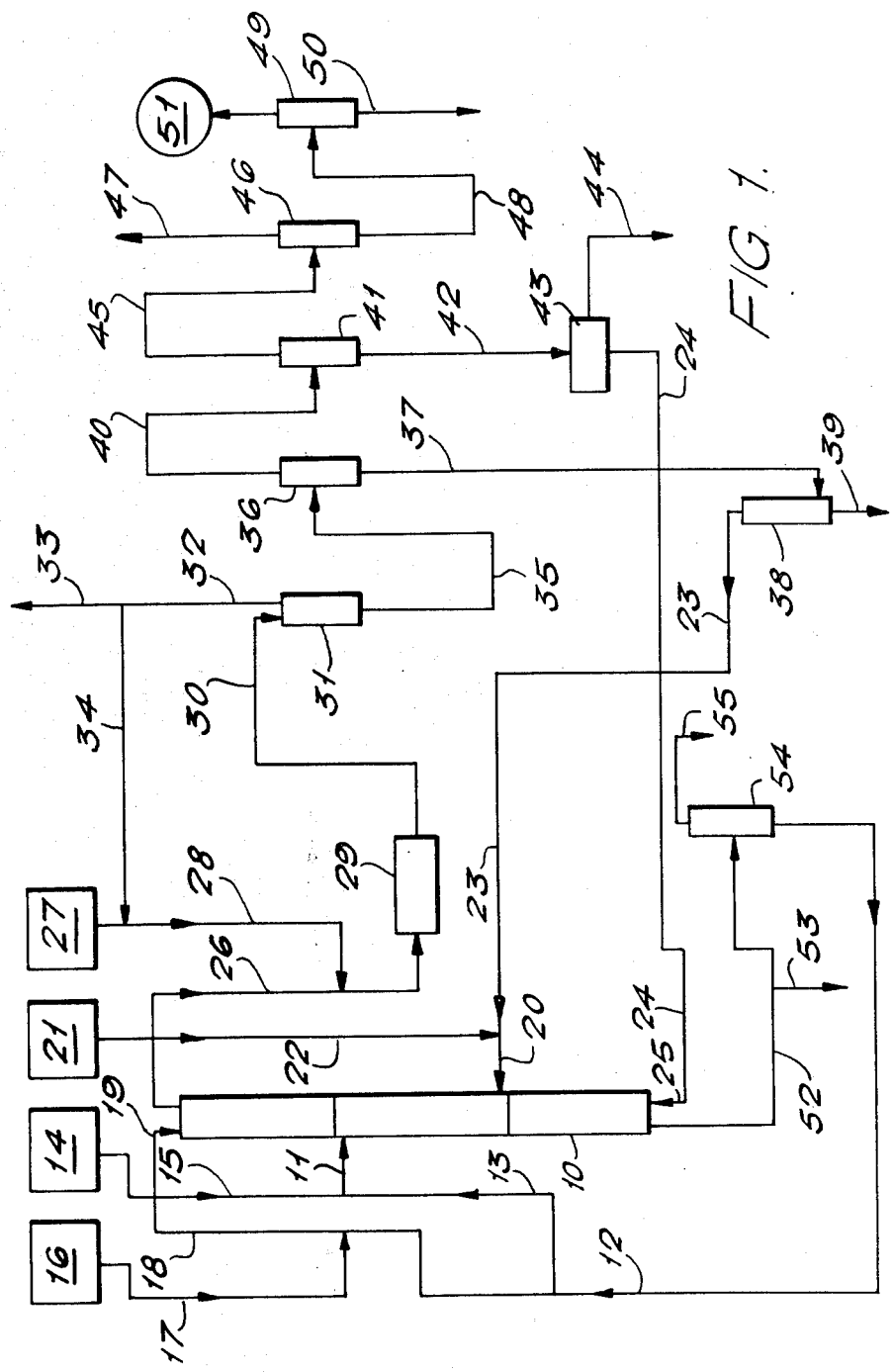
FIG. 1 is a flow sheet for the production of propylene oxide.

Referring now to FIG. 1 of the drawings it will be seen that the plant comprises a three-section extraction column 10 to which is fed via an inlet 11 at the top of the centre section an aqueous phase comprising dilute sulphuric acid from recycle lines 12 and 13 and hydrogen peroxide from peroxide storage tank 14 via peroxide supply line 15. The upper section of the column 10 functions as an acid backwash and for this purpose dilute sulphuric acid from the recycle line 12 is mixed with make-up acid from storage tank 16 supplied via line 17 and is fed by a line 18 to an inlet 19 at the top of the column 10. At the bottom of the centre section of the extraction column 10 is an inlet 20 for an organic phase comprising a solution of propionic acid in propylene dichloride and this is supplied from organic storage tank 21 via line 22 and first organic recycle line 23. The lower section of the extraction column 10 constitutes a stripper section and for this purpose is supplied with recycled propylene dichloride which is fed from a second organic recycle line 24 to an inlet 25 at the bottom of column 10.

An organic solution of perpropionic acid in propylene dichloride is withdrawn from the column 10 through line 26, is mixed with propylene supplied from propylene storage tank 27 via line 28 and is fed to a reactor 29.

From the reactor 29, the reaction mixture is taken by line 30 to a stripping unit 31 in order to remove all traces of unreacted propylene. The propylene is withdrawn from unit 31 through line 32 and a portion is passed to purge through line 33 and portion is pumped back through line 34 to join line 28.

The liquid from the stripping unit 31 is passed by a line 35 to a series of four distillation columns. From the first distillation column 36 the heavy fraction is withdrawn through line 37 and passed to a solvent purification column 38. In this column 38 the solvent mixture from line 37 is distilled in order to produce a light fraction which comprises a solution of propionic acid in propylene dichloride which is withdrawn from the column 38 through the line 23 previously referred to as the organic recycle line. The heavy fraction from the solvent purification column 38 is passed to waste through line 39 as a purge. Some or all of the flow in line 37 can be passed directly to line 23, by-passing the purification column 38.

The light fraction from the distillation column 36 is taken by line 40 and passed to second distillation column 41. The heavy fraction from the distillation column 41 is taken by a line 42 to a decanter 43 which separates out an aqueous phase which is passed to waste through line 44. The organic phase from the decanter 43 is taken by the second organic recycle line 24 to be passed back to the extraction column 10. The light fraction from the second distillation column 41 is taken by line 45 to the third distillation column 46 and this column is operated to withdraw a light fraction through a line 47 and pass it to waste. This fraction is in fact substantially acetaldehyde. The heavy fraction from the distillation column 46 is taken by a line 48 and passed to the final distillation column 49 in which it is finally purified to give a heavy fraction which is withdrawn from the column through line 50 and passed to waste, this heavy fraction being substantially completely propionaldehyde. The product is taken from the column 49 and passed to a propylene oxide storage vessel 51.

Reverting now to the extraction column 10, the aqueous phase therein passes out of the base of the column through a line 52 and a proportion is passed to purge through a line 53, this proportion constituting the acid purge. The remainder in line 52 is passed to a distillation column 54 which serves to recover sulphuric acid. In the distillation column 54 the light fraction constitutes chiefly water and is passed to waste through line 55 whilst the heavy fraction constitutes recycle sulphuric acid and is withdrawn from the column 54 by the line 12 and is passed back to the extraction column 10 as previously described.

In order to more fully understand the operation of the plant above described, reference should now be made to Tables III and IV which show the mass flow (in kilogrammes/hour) in various parts of the plant described. It will be seen that approximately 70% hydrogen peroxide is used. If 86% hydrogen peroxide were used the only difference would be a reduction of 5 kg/hr water in the raw material stream flowing in line 14 and a corresponding reduction in the water purge from line 55.

TABLE III

| | Raw Material Streams | | | | Recycle Streams | | | |
|---|---|---|---|---|---|---|---|---|
| | 14 | 16 | 21 | 27 | 12 | 23 | 24 | 34 |
| Sulphuric acid | | 1.55 | | | 29.45 | | | |
| Water | 8.41 | 0.03 | | | 15.73 | | 0.32 | |
| Hydrogen peroxide | 19.33 | | | | 0.46 | | | |
| Propionic acid | | | 1.74 | | 0.10 | 60.21 | | |
| Propylene dichloride | | | 0.87 | | | 186.73 | 53.56 | |
| Propylene | | | | 23.70 | | | | 6.73 |
| Others | | | | 0.09 | | | | |
| Perpropionic acid | | | | | 0.01 | | | |

TABLE IV

| | Purge Streams | | | | | | | Product Stream |
|---|---|---|---|---|---|---|---|---|
| | 33 | 39 | 44 | 47 | 50 | 53 | 55 | 51 |
| Sulphuric Acid | | 0.04 | | | | 1.55 | | |
| Water | | | 1.30 | | | 1.39 | 15.73 | 0.0005 |
| Hydrogen peroxide | | | 0.37 | | | 0.02 | | |
| Propionic Acid | | 1.24 | | | | 0.01 | | |
| Propylene dichloride | | 0.74 | | | | | 0.02 | 0.0004 |
| Propylene | 0.60 | | | | | | | |
| Others | 0.29 | | | | | | | |
| Perpropionic Acid | | | | | | 0.01 | | |
| Glycols | | 0.35 | | | | | | |
| Propylene Oxide | | | | 0.30 | 0.06 | | | 31.21 |
| Acetaldehyde | | | | 0.12 | | | | 0.0006 |
| Propionaldehyde | | | | | 0.02 | | | 0.0003 |

Figure 2:
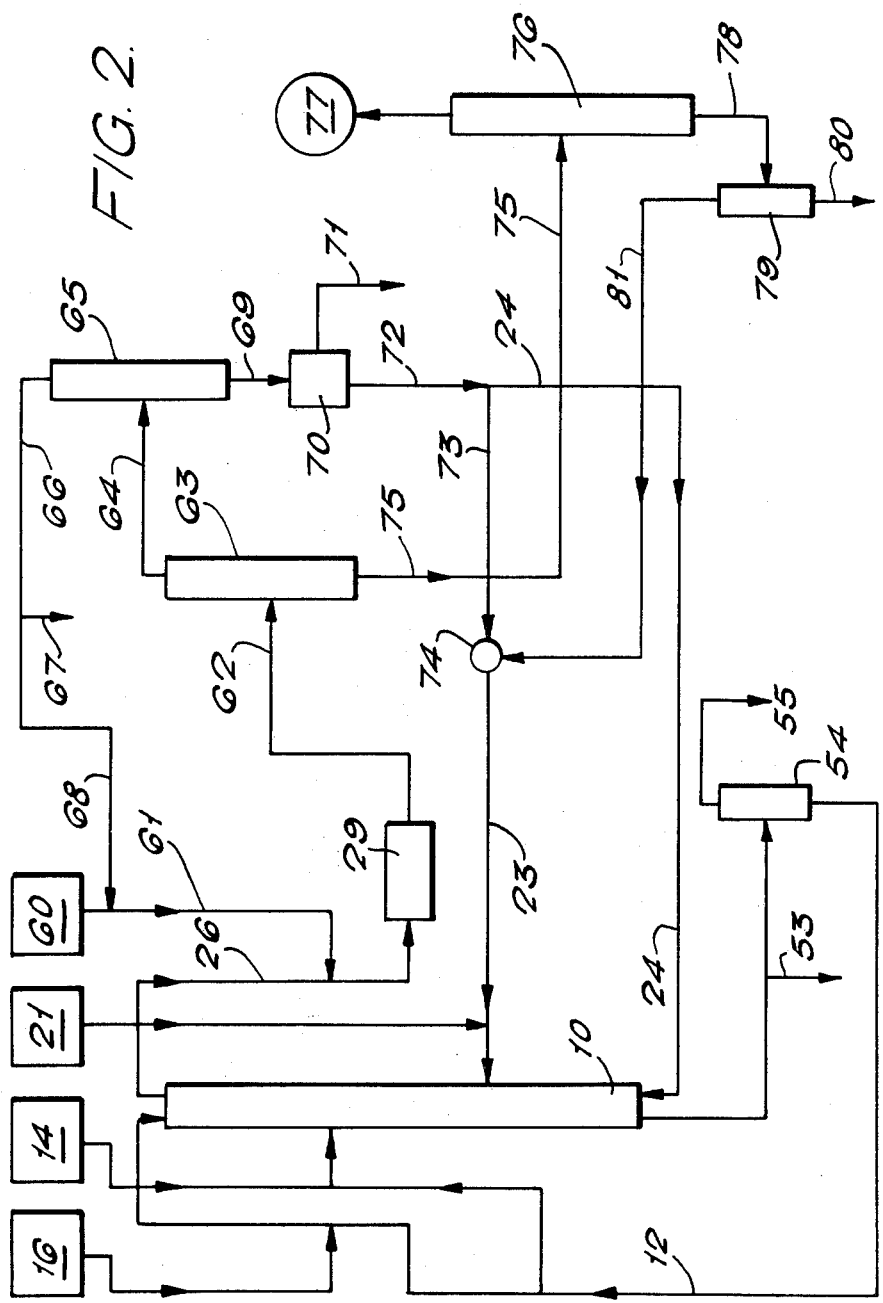
FIG. 2 is a flow sheet for the production of epichlorohydrin.

The plant to produce epichlorohydrin from allyl chloride is illustrated in FIG. 2 and it will be seen that it differs from that to produce propylene oxide chiefly in the purification stages. Thus referring to FIG. 2 the organic solution of perpropionic acid in line 26 is mixed with allyl chloride supplied from allyl chloride storage tank 60 via line 61 and is fed to the reactor 29.

From the reactor 29 the reaction mixture is taken by line 62 to a fractionating column 63 which separates as a light fraction allyl chloride, propylene dichloride and water. This light fraction passes through line 64 to a second fractionating column 65 where allyl chloride is separated as a light fraction and is withdrawn through line 66. A portion of the allyl chloride in line 66 is passed to purge through line 67 and a portion is passed back through line 68 to joint line 61.

The heavy fraction from the second column 65 is taken by line 69 to a decanter 70 which separates out an aqueous phase which is passed to waste through line 71. The organic phase from the decanter 70 is taken by line 72 and is split between the second organic recycle line 24 leading to the bottom of the extraction column 10 and a line 73 leading to a mixing device 74.

The heavy fraction from the first column 63 passes via line 75 to a distillation column 76. The light fraction from the column 76 forms the product and is passed to a product storage tank 77, whilst the heavy fraction passes via line 78 to column 79. In the column 79 the heavy fraction from the column 76 (mainly propionic acid) is distilled in order to produce a light fraction free of heavy impurities. The heavy fraction from the column 79 is passed to waste through line 80 as a purge.

The light fraction from the column 79 is taken via a line 81 to the mixer device 74, where it is mixed with the solution from line 73 and passed into line 23, previously referred to as the organic recycle line.

The remainder of the plant in FIG. 2 is essentially as described with reference to FIG. 1 and in order to more fully understand its operation, reference should now be made to Tables V and VI which show the mass flow (in kilogrammes/hour) in various parts of FIG. 2 described, in so far as they differ from those in FIG. 1.

TABLE V

|  | Raw Material Streams | | | | Recycle Streams | | | |
| --- | --- | --- | --- | --- | --- | --- | --- | --- |
|  | 14 | 16 | 21 | 60 | 12 | 23 | 24 | 68 |
| Sulphuric acid |  | 1.55 |  |  | 29.45 |  |  |  |
| Water | 8.41 | 0.03 |  |  | 15.73 |  | 0.52 |  |
| Hydrogen peroxide | 19.33 |  |  |  | 0.46 |  |  |  |
| Propionic acid |  | 1.74 |  |  | 0.10 | 61.80 |  |  |
| Propylene dichloride |  |  | 0.87 |  |  | 167.6 | 72.7 |  |
| Allyl chloride |  |  |  | 43.67 |  |  |  | 36.73 |
| Perpropionic acid |  |  |  |  |  | 0.01 |  |  |

TABLE VI

|  | Purge Streams | | | | | Product Stream |
| --- | --- | --- | --- | --- | --- | --- |
|  | 67 | 71 | 80 | 53 | 55 | 77 |
| Sulphuric acid |  |  | 0.04 | 1.55 |  |  |
| Water |  | 1.30 |  | 1.39 | 15.73 |  |
| Hydrogen peroxide |  | 0.37 |  | 0.02 |  |  |
| Propionic acid |  |  | 1.24 | 0.01 |  |  |
| Propylene dichloride |  |  | 0.01 |  | 0.02 | 0.001 |
| Allyl chloride | 1.06 |  |  |  |  |  |
| Others | 0.39 |  |  |  |  |  |
| Perpropionic acid |  |  | 0.01 |  |  |  |
| Glycols |  | 0.95 |  |  |  |  |
| Epichlorhydrin |  |  |  |  |  | 49.27 |

Turning now to FIG. 3 this is a plant for the production of propylene oxide in accordance with the invention, using propionic acid as the carboxylic acid and benzene as the solvent. It will be seen that the plant has three series-connected stages of countercurrent extraction and five series-connected stages of distillation in the purification train. It will be understood that in a practical plant, two or more of these series-connected stages may be combined in a single column. However for the sake of clarity they are illustrated as separate stages.

The extraction section which, in accordance with the invention, also includes the reaction section comprises columns 101, 102 and 103 all arranged to operate in countercurrent. Step (c) of the present invention takes place mainly in the column 102, which is the main reaction column. To that end hydrogen peroxide is supplied at the head of the column by a line 104 from a storage tank 105. Aqueous sulphuric acid is supplied at the head of the column 102 by a line 106 and in accordance with step (d) of the invention this is a recycle phase. Aqueous sulphuric acid is also supplied to the head of the column 102 by a line 107 taken from the base of the column 103. The hydrogen peroxide, sulphuric acid and water supplied by the lines 104, 106 and 107 together constitute the aqueous phase of step (a). An organic solution is supplied to the base of the column 102 by a line 108 from the top of the column 101. Fresh propionic acid in benzene from a make-up storage tank 110 is also supplied to the base of the column 102 by a line 109. Finally a recycle phase comprising propionic acid in benzene in accordance with step (g) is supplied to the base of the column 102 by a line 111. The carboxylic acid and organic solvent provided by the lines 108, 109 and 111 to the base of the column 102 together constitute the organic phase in accordance with step (b). Since the organic phase is lighter than the aqueous phase, these will pass in countercurrent through the column 102 in accordance with step (c) and will react in order to produce perpropionic acid.

Thus an aqueous solution comprising sulphuric acid and water is taken from the base of the column 102 by a line 112 and is taken to the top of the column 101 which functions as an organic back-wash column. Solvent, substantially free of propionic acid, is supplied to the base of the back-wash column 101 by a line 113 and passes in countercurrent to the aqueous solution in order to back-wash it and strip from it as much propionic acid as possible. The conditions are such that the aqueous effluent from the back-wash column 101 which is taken by line 114 contains substantially no carboxylic acid, peracid or hydrogen peroxide. The organic solution from the column 102 comprises a solution of perpropionic acid in benzene and is taken by a line 115 to the base of the column 103 which acts as an aqueous back-wash column. To that end, the head of the column 103 is provided with fresh sulphuric acid in aqueous solution by a line 116 from a makeup tank 117, the sulphuric acid passing out of the column 103 by the line 107. The function of this aqueous acid back-wash is to strip the organic phase flowing through the column 103 and remove from it all the dissolved hydrogen peroxide.

The organic solution leaves the acid back-wash column 103 by a line 118 and is taken to a drying column 119 where it is distilled in order to remove sufficient azeotrope as an overhead fraction through a line 120 to remove substantially all the water contained in the organic solution. The heavy fraction from the column 119 is taken by a line 121 as a substantially anhydrous solution.

The substantially dry organic solution is now fed by the line 121 to a reactor 122 which is conveniently illustrated as a column, although in practice a long tubular reactor would be preferred. Propylene is also fed to this reactor by a line 123 from a storage vessel 124. It will be appreciated that under normal conditions of temperature and pressure, propylene is a gas and therefore the reactor 122 is operated under pressure in order that the propylene should be kept in solution in the organic solution. The propylene reacts with the perpropionic acid in the reactor 122 to give propylene oxide and propionic acid in accordance with step (e). This product mixture is taken by a line 125 to a first distillation column 126 and in this column any unreacted propylene is distilled off as a light fraction and is passed by a line 127 to a condenser 128. In the condenser 128 the propylene is condensed and is fed by a line 129 back to the reactor 122. Any uncondensible gases are passed to waste through a line 130.

The heavy fraction from the first distillation column 126 is taken by a line 131 to a second distillation column 132 where it is split into two fractions. The heavy fraction is taken by a line 133 and comprises a solution of propionic acid in benzene in accordance with step (f). The light fraction is taken by a line 134 to a third distillation column 135. The heavy fraction from the distillation column 135 is taken by a line 136 and comprises essentially benzene without any substantial amount of dissolved propionic acid. The light fraction is taken by a line 137 to a fourth distillation column 138. This feed comprises substantially pure propylene oxide, that is to say propylene oxide which has had unreacted propylene, benzene and propionic acid removed from it. It now undergoes a first distillation stage of purification in the column 138, the low boiling impurities being withdrawn and passed to waste through a line 139. The heavy fraction is taken by a line 140 to the second purification stage constituted by the fifth distillation column 141 where the light fraction constitutes the product and is withdrawn through a line 142 whilst the high boiling impurities are passed to waste through a line 143.

As will be apparent there are a number of recycle streams and reactant purification is conveniently effected on the recycle streams. Thus the line 136 from the third purification column carries benzene together with any water which has been produced subsequent to the drying distillation column 119. Although the recycle stream can tolerate a reasonable amount of water, it is desirable to remove any excess water and the line 136 therefore leads to a decanter 144 where this recycle stream is permitted to separate into two phases and the lower phase, being chiefly water, is discarded to waste through a line 145. The benzene is taken from the decanter 144 by the line 113 previously referred to.

The stream in the line 133 comprises essentially propionic acid in benzene and this is to be recycled in accordance with step (g). However, since some degradation products will collect in this stream, the line 133 leads to a distillation column 146 from which the light fraction is taken by the line 111 previously referred to. The heavy fraction is discarded to waste through a line 147.

The benzene/water azetrope azeotrope the line 120 is taken to a decanter 148 where it is allowed to separate into two phases. The lower phase, being chiefly water, is discarded to waste through a line 149. The upper phase, being chiefly benzene, is taken by a line 150 to join the line 113.

The aqueous solution taken from the base of the organic back-wash column 101 by the line 114 is to be utilised, at least in part, in accordance with step (d) but it will be appreciated that this aqueous solution contains too much water for direct replacement as step (a) since the original hydrogen peroxide content has reacted to give water. The line 114 therefore leads to a distillation column 151 where it is distilled in order to provide a light fraction which is substantially water and which is taken off by a line 152 and passed to waste. The heavy fraction from the column 151 comprises sulphuric acid in water and could conveniently be re-distilled in order to remove heavy boiling impurities which would otherwise accumulate in the aqueous phase. However in the preferred arrangement a bleed from the aqueous phase is taken from the heavy fraction from the distillation column 151 by a line 153 and the remainder is passed back by the line 106 to the head of the column 102.

The columns 101, 102 and 103 preferably operate at normal temperature, that is to say without any added heating or cooling, and under normal hydrostatic pressure. The drying column 119 conveniently operates at a temperature of 45°–50° C. and a pressure of 250–350 torr. The reactor 122 conveniently operates at 90°–110° C. and under a pressure of 12 atm. in order to keep the propylene in solution. The first distillation column 126 can conveniently operate at normal temperatures and normal pressures since this is sufficient to cause unreacted propylene to boil off and the condenser 128 conveniently operates at the slightly increased pressure of 10 psig. and is in addition cooled to −10° C. The second, third, fourth and fifth distillation columns, 132, 135, 138 and 141 all conveniently operate at atmospheric pressure and at temperatures of 65° C., 70° C., 80° C. and 90° C. respectively. The columns 146 and 151 operating in the recycle streams can conveniently operate at temperatures and pressures of 80° C./1 atm. and 130° C./100 torr. respectively.

It will be apparent that the differences between the plant of FIG. 1 and FIG. 3 are marginal and that the prime difference resides in the fact that benzene is used as the solvent and that therefore, because of the greater solubility of water in benzene than in propylene dichloride, an additional drying stage is desirable. As to efficiency of operation, with an input of hydrogen peroxide and propionic acid to column 102 in the molar ratio 1:1.4 an overall conversion efficiency of 91.5% was obtained.

We claim:
1. A continuous process for the production of a peracid in an organic solvent comprising the steps of:
    (a) providing an aqueous phase comprising sulphuric acid, hydrogen peroxide and water;
    (b) providing an organic phase comprising an organic solvent and an unsubstituted monocarboxylic acid having at least two but less than six carbon atoms; and
    (c) contacting said aqueous and organic phases countercurrently to produce an aqueous solution comprising sulphuric acid and water and an organic product solution comprising organic solvent and a peracid corresponding to said carboxylic acid.
2. The process of claim 1, including the added step of:
    (d) utilising at least a portion of said aqueous solution to provide at least a portion of the aqueous phase of step (a).
3. The process of claim 2, wherein the aqueous solution is concentrated by the removal of water prior to being used as a portion of the aqueous phase.
4. The process of claim 1, wherein the carboxylic acid comprises acetic or propionic acid.
5. The process of claim 1, wherein the solvent is selected from the group consisting of chlorinated hydrocarbons. hydrocarbons, esters and nitrocompounds.
6. The process of claim 5, wherein the solvent is selected from the group consisting of chlorinated aliphatic hydrocarbons, chlorinated aromatic hydrocarbons and chlorinated cyclo aliphatic hydrocarbons.

7. The process of claim 5, wherein the solvent is selected from the group of non-chlorinated hydrocarbons consisting of aliphatic hydrocarbons, cyclo aliphatic hydrocarbons, aromatic hydrocarbons and alkyl aryl hydrocarbons.

8. The process of claim 5, wherein the solvent is selected from the group consisting of propylene dichloride and benzene.

9. The process of claim 1, wherein the proportion of sulphuric acid in the aqueous phase is between 30% and 60% by weight.

10. The process of claim 1, wherein the proportion of hydrogen peroxide in the aqueous phase is between 10% and 35% by weight.

11. The process of claim 1, wherein the proportion of carboxylic acid in the organic phase is between 15% and 30% by weight.

12. The process according to claim 1, wherein the relative volumes and concentrations of the organic and aqueous phases are such that the molar ratio of hydrogen peroxide to carboxylic acid is between 1:0.5 to 1:4.

13. A continuous process for the production of a peracid in an organic solvent comprising the steps of:
(a) providing an aqueous phase comprising sulphuric acid, hydrogen peroxide, and water;
(b) providing an organic phase comprising an organic solvent, other than a chlorinated hydrocarbon, and an unsubstituted monocarboxylic acid having at least two but less than six carbon atoms; and
(c) continuously contacting said aqueous and organic phases countercurrently to produce an aqueous stream comprising sulphuric acid and water and a product stream comprising organic solvent and a peracid corresponding to said carboxylic acid.

14. A continuous process for the epoxidation of an alkene by reaction with a peracid to produce an oxirane, comprising the steps of:
(a) providing an aqueous phase comprising sulphuric acid, hydrogen peroxide and water;
(b) providing an organic phase comprising an organic solvent and an unsubstituted monocarboxylic acid having at least two but less than six carbon atoms;
(c) contacting said aqueous and organic phases countercurrently to produce an aqueous solution comprising sulphuric acid and water and an organic product solution comprising organic solvent and a peracid corresponding to said carboxylic acid; and
(d) reacting at least a portion of the peracid in said organic product solution and an alkene to produce a product mixture comprising oxirane, carboxylic acid, and organic solvent.

15. A continuous process for the epoxidation of an alkene by reaction with a peracid to produce an oxirane, comprising the cyclic steps of:
(a) providing an aqueous phase comprising sulphuric acid, hydrogen peroxide and water;
(b) providing an organic phase comprising an unsubstituted monocarboxylic acid having at least two but less than six carbon atoms and an organic solvent;
(c) contacting said aqueous and organic phases countercurrently to produce an aqueous solution comprising sulphuric acid and water and an organic solution comprising peracid and organic solvent;
(d) utilising at least a portion of said aqueous solution to provide at least a portion of the aqueous phase of step (a);
(e) reacting at least a portion of the peracid of said organic solution and an alkene to produce a product mixture comprising oxirane, carboxylic acid and organic solvent;
(f) effecting distillation of said product mixture to produce a product phase comprising the oxirane and a recycle phase comprising carboxylic acid and organic solvent; and
(g) utilising at least a portion of said recycle phase to form at least a portion of the organic phase of step (b).

16. The process of claim 15, wherein the alkene comprises propene.

17. The process of claim 15, wherein the alkene is in stoichiometric excess.

18. The process of claim 15, wherein the alkene comprises allyl alcohol and the carboxylic acid comprises acetic acid, thereby to produce glycidol.

19. The process of claim 15, wherein the alkene comprises propylene or butylene and the carboxylic acid comprises propionic acid, thereby to produce propylene or butylene oxide.

20. A continuous process for the epoxidation of an alkene by reaction with a peracid to produce an oxirane, comprising the cyclic steps of:
(a) providing an aqueous phase comprising sulphuric acid, hydrogen peroxide and water;
(b) providing an organic phase comprising an unsubstituted monocarboxylic acid having at least two but less than six carbon atoms and an organic solvent other than a chlorinated hydrocarbon;
(c) contacting the said aqueous and organic phases countercurrently to produce an aqueous solution comprising sulphuric acid and water and an organic solution comprising peracid and organic solvent;
(d) utilising at least a portion of said aqueous solution to provide at least a portion of the aqueous phase of step (a);
(e) reacting at least a portion of the peracid of said organic solution and an alkene to produce a product mixture comprising oxirane, carboxylic acid and organic solvent;
(f) effecting distillation of said product mixture to produce a product phase comprising the oxirane and a recycle phase comprising carboxylic acid and organic solvent; and
(g) utilising at least a portion of said recycle phase to form at least a portion of the organic phase of step (b).

* * * * *